United States Patent [19]

Maeda et al.

[11] Patent Number: 5,021,406

[45] Date of Patent: Jun. 4, 1991

[54] 2-PYRANONE DERIVATIVE AND PROCESS FOR PRODUCTION THEREOF

[75] Inventors: Mitsuru Maeda, Ohtsu; Tohru Kodama, Takatsuki; Sumio Asami, Ibaraki; Norihide Amano, Takatsuki; Takaaki Kusumi, Suita; Hidekazu Hosono, Yokohama, all of Japan

[73] Assignee: Suntory Limited, Osaka, Japan

[21] Appl. No.: 309,673

[22] Filed: Feb. 13, 1989

[30] Foreign Application Priority Data

Feb. 13, 1988 [JP] Japan .................... 63-30069

[51] Int. Cl.$^5$ ..................... A61K 31/665; C07F 9/143
[52] U.S. Cl. ........................ 514/99; 549/222
[58] Field of Search ................... 549/222, 293; 514/99

[56] References Cited

U.S. PATENT DOCUMENTS 4,575,500 3/1986 Burg et al. .......................... 549/222
4,578,383 3/1986 Stampwala et al. ................ 549/222

FOREIGN PATENT DOCUMENTS 0128651 12/1984 European Pat. Off. .

Primary Examiner—Richard L. Raymond
Assistant Examiner—Mark W. Russell
Attorney, Agent, or Firm—Burns, Doane, Swecker & Mathis

[57] ABSTRACT

A 2-pyranone derivative represented by the formula (I):

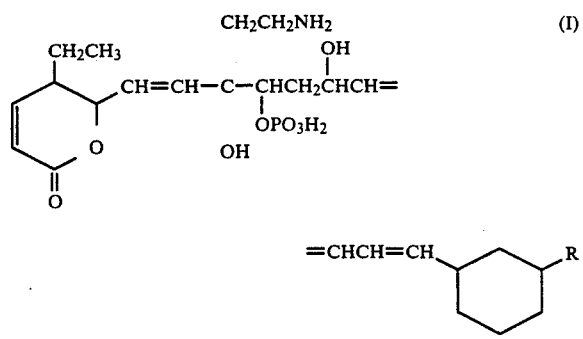

wherein R represents a hydrogen atom, or a linear, branched alkylcarbonyloxy, or cyclo-alkylcarbonyloxy group having 3 to 10 carbon atoms, and salts thereof; a process for the production of the above-mentioned 2-pyranone derivative (I), comprising the steps of culturing a microorganism belonging to the genus Streptomyces and capable of producing the derivative, to produce the derivative, and recovering the produced derivative from the cultured product; a biocidal composition comprising the above-mentioned 2-pyranone derivative (I); and a microorganism belonging to the genus Stretromyces and capable of producing the above-mentioned 2-pyranone derivatives.

13 Claims, 1 Drawing Sheet

2-PYRANONE DERIVATIVE AND PROCESS FOR PRODUCTION THEREOF

BACKGROUND OF THE INVENTION

1 Field of the Invention

The present invention relates to novel 2-pyranone derivatives and a process for production thereof, and to antimicrobial compositions containing the derivative. The present novel 2-pyranone derivatives exhibit an antimicrobial activity especially to plant pathogenic fungi at a very low concentration, and therefore, are useful as an active ingredient for an agricultural biocidal composition.

2. Description of the Related Art

U.S. Pat. No. 4,578,383 corresponding to EP publication No. 0,087,021, and EP publication No. 0,128,651 describe a compound having a basic structure of the formula (I) of the present invention but having a hydrogen atom or a hydroxyl group at the 5-position of the pyranone ring, rather than the ethyl group as in the present compound, and having a 1-propenyl or 3-hydroxy-1-propenyl at a position most distant from the pyranone ring, rather than a cyclohexyl ring as in the present compound. However, these compounds are remarkably different in structure from that of the present compound having an ethyl group at the 5-position of the pyranone ring and a cyclohexyl ring structure at the position most distant from the pyranone structure. Moreover, the above-mentioned publications do not suggest that a microorganism belonging to Streptomyces produces the present compounds.

U.S. Pat. No. 4,575,500 discloses a compound having a structure similar to the present formula (I), but having a cyclohexenone structure rather than the pyranone ring of the present invention.

SUMMARY OF THE INVENTION

The present invention is intended to provide new biocidal compounds which do not exhibit disadvantageous side effects on agricultural plants, and are useful for the prevention and control of *Botrytic cinerea* which can be parasitic on a very wide range of plants such as of cucumber, tomato, eggplant, strawberry, lettuce, udo (*Aralia cordata*), and onion at low temperatures and high moisture conditions.

To accomplish the above, the present inventors attempted to isolate from nature a microorganism which produces biologically active compounds suppressing the gray mold, and found that an actinomyces belonging to the genus Streptomyces produces in a culture broth substances which exhibit a growth-preventing effect on fungi including dermatophytes and plant pathogenic fungi at a very low concentration. The present inventors further isolated and purified the substance and determined a structure thereof, and confirmed that the purified substance strongly suppresses the gray mold.

Accordingly, the present invention provides a 2-pyranone derivative represented by the formula (I):

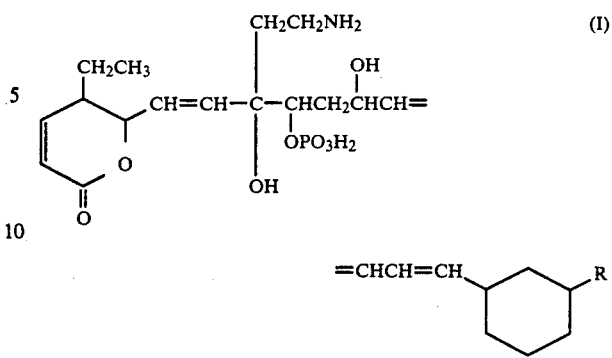

wherein R represents a hydrogen atom, or a linear or branched alkyl carbonyloxy, or cyclo-alkyl carbonyloxy group having 3 to 10 carbon atoms, and salts thereof.

The present invention also provides a process for the production of a 2-pyranone derivative (I), comprising the steps of culturing a microorganism belonging to the genus Streptomyces and capable of producing the derivative, to produce the derivative, and recovering the produced derivative from the cultured product.

Moreover, the present invention provides a biocidal composition comprising the above-mentioned 2-pyranone derivative. Still further, the present invention provides a microorganism belonging to the genus Streptomyces and capable of producing the above-mentioned 2-pyranone derivatives.

DESCRIPTION OF THE PREFERRED EMBODIMENT

Figure 1:
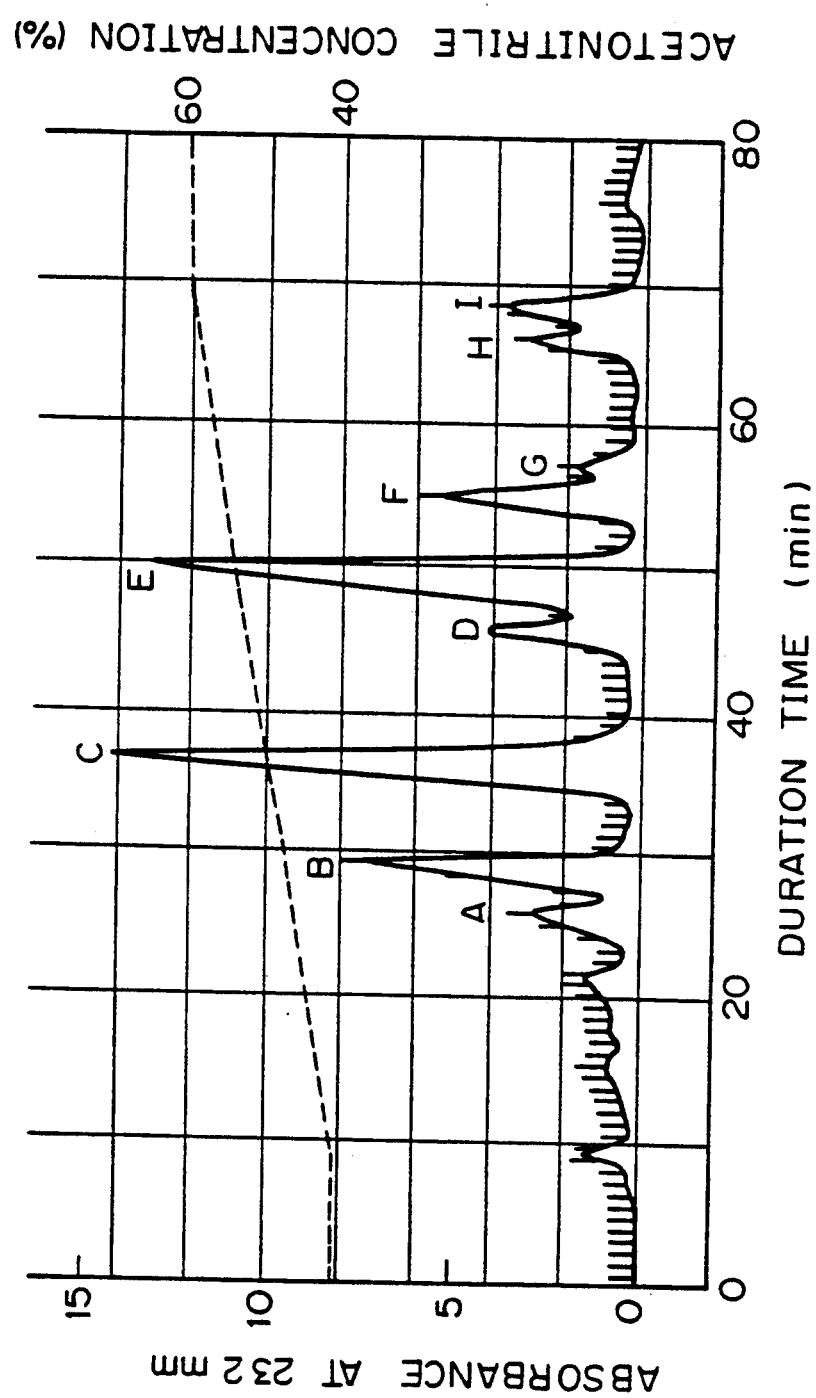
FIG. 1 represents an elution profile where components in a concentrated supernatant from a culture broth were separated by high performance liquid chromatography.

In the above-mentioned formula (I), the alkylcarbonyloxy group is preferably butyryloxy, isobutyryloxy, isovaleryloxy, 2-methylbutyryloxy, cyclohexylcarbonyloxy, 4-methylhexanoyloxy, 6-methylheptanoyloxy, or octanoyloxy.

In the present invention, the producer microorganism is any microorganism belonging to the genus Streptomyces and capable of producing the present 2-pyranone derivatives.

Such a microorganism can be obtained by isolating microorganisms belonging to Streptomyces from microbial sources such as soil, by a conventional procedure for the isolation of actinomyces, and selecting a microorganism organism which produces a substance having an antimicrobial activity against *Botrytic cinerea*. A producer strain of the present invention thus obtained, *Streptomyces platensis* SAM-0654, was deposited with the Fermentation Research Institute, Agency of Industrial Science and Technology on January 22, 1988, as FERM BP-1668.

The strain SAM-0654 has the following taxonomical properties.

1. Morphology

An aerial mycelium shows simple branches, and at the top thereof, a spiral spore chain comprising 10 to 50 or more spores is formed. The spore is semispherical (crescent), has a length of 0.6 to 1.0 μm and a width of 0.3 to 0.4 μm, and has a smooth surface.

2. Cultural characteristics on various media

The appearance of a culture on various media is set forth in Table 1. The observation was carried out after culturing at 28° C. for 21 days.

TABLE 1

| Culture media | Growth | Aerial *mycelium* | | Vegetative *mycelium* | Soluble pigment | Other appearance |
|---|---|---|---|---|---|---|
| Yeast extract - Malt extract Agar (ISP-2) | Good | Abundant | White-Light yellowish-Gray | Brown | Yellow | Hygroscopic |
| Oat meal agar (ISP-3) | Good | Abundant | White-Gray | Yellowish brown-Brown | Yellow | Hygroscopic |
| Inorganic salts - Starch agar (ISP-4) | Good | Abundant | White-Light yellowish-Gray | Yellow-Yellowish brown | Light yellow | Hygroscopic |
| Glycerol - Asparagine agar (ISP-5) | Good | Abundant | White-Light yellowish gray | Orange-Yellowish brown | Yellow | |
| 1/10 V-8 agar | Good | Moderate | White-Gray | Deep greenish gray | — | Hygroscopic |
| Yeast extract - Starch agar | Good | Abundant | White | Yellow-Light yellowish brown | Light yellow | No spore formation |
| 1/10 Potato - Carrot agar | Good | Moderate | White-Light gray | White-Light yellow | — | Hygroscopic |
| Calcium malate agar (+ Glycerol) | Good | Poor | White | Yellow | — | — |

3. Physiological properties

| | | |
|---|---|---|
| (1) | Scope of growth temperature | 20° C. to 37° |
| (2) | Liquification of gelatine | negative |
| (3) | Hydrolysis of starch | positive |
| (4) | Coagulation of skim milk (37° C.) | negative |
| (5) | Peptonization of skim milk (37° C.) | negative |
| (6) | Production of melanoid pigments | |
| | Tryptone-yeast extract agar medium | negative |
| | Tyrosine agar medium | negative |
| | Peptone-yeast extract-iron agar medium | negative |
| (7) | Nitrate reduction | negative |
| (8) | Utilization of carbon sources | |

| | | | |
|---|---|---|---|
| L-arabinose | − | L-rhamnose | − |
| D-xylose | ± | raffinose | + |
| D-glucose | ++ | D-mannitol | ++ |
| D-fructose | + | lactose | − |
| sucrose | ++ | salicin | − |
| inositol | ++ | cellulose | − |

4. Chemotaxonomical properties (1) 2,6-diaminopimelic acid

Whole-cell hydrolyzates of SAM 0654 contained L,L-2,6-diaminopimelic acid.

(2) Quinone system

The strain SAM 0654 has melaquinone-9($H_6$) and melaquinone −9($H_8$) as major quinones.

From the above-mentioned taxonomical properties, the present strain SAM-0654 is considered to be an actinomyces belonging to the genus Streptomyces. Comparison of the present strain with the known species of the genus Streptomyces, on the basis of the above-mentioned taxonomical properties, revealed that the present strain is most similar to *Streptomyces platensis* (International Journal of Systematic Bacteriology, Vol. 18, pp 360, 1968).

Accordingly, the present strain SAM-0654 was compared with a type strain of *Streptomyces platensis*. i.e., *Streptomyces platensis* JCM 4662, and a summary of the results thereof is given in Table 2.

TABLE 2

| | | | SAM0654 | *Streptomyces platensis* JCM 4662 |
|---|---|---|---|---|
| | | Spore chain | Spiral | Spiral |
| | | Surface and shape of spore | Smooth, subspherical (crescent) | Smooth, subspherical (crescent) |
| Cultural characteristics | Yeast extract - Malt extract agar (ISP-2) | Aerial *mycelium* | White-Gray | Gray |
| | | Vegetative *mycelium* | Brown | Reddish brown |
| | | Soluble pigments | Yellow | Light brown |
| | | Other appearance | Hygroscopic | Hygroscopic |
| | Oat meal agar (ISP-3) | Aerial *mycelium* | White-Gray | Gray |
| | | Vegetative *mycelium* | Yellowish brown | Reddish brown |
| | | Soluble pigments | Yellow | Light brown |
| | | Other appearance | Hygroscopic | Hygroscopic |
| | Inorganic salt - Starch agar (ISP-4) | Aerial *mycelium* | White-Gray | Gray |
| | | Vegetative *mycelium* | Light yellowish brown | Reddish brown |
| | | Soluble pigments | Light yellow | Light brown |
| | | Other appearance | Hygroscopic | Hygroscopic |
| | Glycerol - asparagine agar (ISP-5) | Aerial *mycelium* | Light yellowish gray | Gray |
| | | Vegetative *mycelium* | Yellowish brown | Yellowish brown |
| | | Soluble pigments | Yellow | — |
| | | Other appearance | — | — |
| Production of melanoid pigments | | | negative | negative |
| Liquidification of gelatine | | | negative | negative |
| Hydrolysis of starch | | | positive | positive |

TABLE 2-continued

|  | SAM0654 | *Streptomyces platensis* JCM 4662 |
| --- | --- | --- |
| Coagulation and peptonization of skim milk | negative | negative |
| Utilization of carbon source | Glucose, fructose, sucrose, inositol, raffinose, mannitol | Glucose, fructose, sucrose, inositol, raffinose, mannitol |

As seen from Table 2, properties of the SAM-0654 are very similar to those of *Streptomyces platensis*, and the only difference is the color tone of the vegetative mycelium and soluble pigments. In the type strain of *Streptomyces platensts, Streptomyces platensis* JCM 4662, the color tone of the vegetative mycelium and soluble pigments is reddish; on the other hand in the strain SAM-0654 it is yellowish. Nevertheless, the present inventors consider that these differences are in sufficient to separate the strain SAM-0654 from *Streptomyces platensis*, and therefore identified the strain SAM-0654 as Streptomyces platensis SAM 0654.

For producing the present compound, a producer strain is preferably cultured in a liquid medium under an aerobic condition provided by shaking or by aeration and agitation, although a solid medium may be used. Any medium in which a producer microorganism can grow and produce the present compound may be used, as long as the medium contains a carbon source such as glucose, lactose, glycerol, starch, sucrose, dextrin, molasses and/or organic acids, and a nitrogen source, such as a hydrolyzed protein product such as pepton or casamino acid, meat extract, yeast extract, defatted soybean pellet, corn steep liquor, amino acids, ammonium salts, nitrate or other organic or inorganic nitrogen-containing substances. Inorganic salts, such as various phosphates, magnesium sulfate, and/or sodium chloride may be added to the medium. Moreover, vitamins and nucleic acid-related compounds may be added to accelerate the growth of the strain. Note, in some cases, the addition of an antifoamer such as silicone, propylene glycol derivatives, and soy bean oil may increase the accumulation level of the present compound.

When culturing, preferably a preculture is prepared on a small scale, and the preculture is innoculated to a production culture medium, although direct innoculation to a production culture medium may be used. Culture conditions including culture temperature, pH value of the culture medium, and duration of culture are chosen or controlled so that the conditions provide maximum production of the present compound. Usually, culturing is carried out at 25° C. to 35° C., at pH 5.5 -7.2, under an aerobic condition, for two to three days.

During the culturing, the present compounds are extracellularly accumulated in a culture broth. Therefore, in a preferred embodiment for recovering the products, a culture broth is filtrated or centrifuged to obtain a filtrate or supernatant containing the products, and the desired products are recovered from the filtrate or supernatant. Alternatively, the product can be directly recovered from a culture broth. The recovery process is followed by a disk method using *Aspergillus oryzae* or *Botrytis cinerea* as a test organism, or a cucumber seedling assay described in the examples.

The desired compound is isolated and purified from the culture broth by various procedures chosen according to the nature of the desired compound. Namely, extraction using an organic solvent, such as 1-buthanol, which is immiscible with water and dissolves the desired compound, dissolution in a high polar solvent such as methanol or ethanol, removal of impurities by treatment with hexane or the like, gel filtration through Sephadex, ion exchange chromatography on an ion exchange resin, Sephadex ion exchanger or the like, or adsorption chromatography on active carbon, silica gel or Amberlite XAD-1 or -2, or a combination thereof, can be used to isolate and purify the desired compound. As especially preferable adsorbents, Diaion HP-20 (Mitsubishi Chemical Industry Ltd.), Sepabeads FP-DA13 (Mitsubishi Chemical Industry Ltd.), YMC-$C_{18}$ (Yamamura Chemical Laboratories Co. Ltd.), and a combination thereof, are mentioned. Note, since a culture broth from the producer strain contains more than ten analogues, separation and purification of each active component can be most effectively carried out by high performance liquid chromatography.

FIG. 1 represents a chromatogram of the separation of components shown by absorbance at 232 nm, obtained using a column YMC-$C_{18}$ (50 mm of an inner diameter and 300 mm of a length, Yamamura Chemical Laboratories Co. Ltd.) and a gradient elution with 40% to 60% acetonitrile containing 0.1% formic acid at a flow rate of 32 ml/minute. Each peak was fractionated, the component was purified, and each component was found to have the following structure (I):

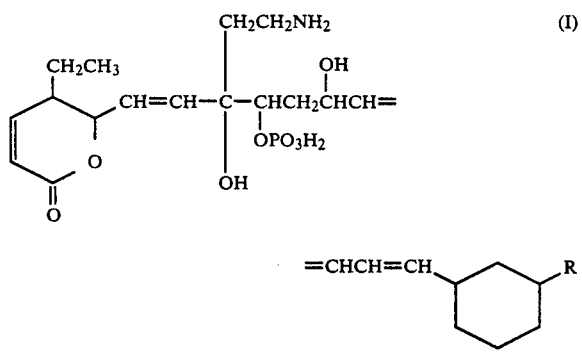

Referring to the above-mentioned general formula and FIG. 1;

Peak A in FIG. 1 represents a compound (I-a) of the present invention, wherein R in the formula (I) is a hydrogen atom;

Peak B represents a mixture of a compound (I-b), wherein R is n-butyryloxy, and a compound (I-c), wherein R is isobutyryloxy;

Peak C represents a mixture of a compound (I-d), wherein R is isovaleryloxy, and a compound (I-e), wherein R is 2-methylbutyryloxy;

Peak E represents a compound (I-f), wherein R is cyclohexylcarbonyloxy;

Peak F represents a compound (I-g), wherein R is 4-methylhexanoyloxy;

Peak H represents a compound (I-h), wherein R is 6-methylheptanoyloxy; and

Peak I represents a mixture of a major compound (I-i), wherein R is octanoyloxy, and a compound (I-j), wherein R is

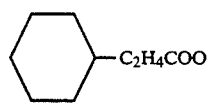

In addition to the above-mentioned compounds, it was found that minor compounds wherein R is, for example, propionyloxy, valeryloxy, or 4-methylvaleryloxy, are present, on the basis of NMR spectra and Mass spectra.

The present compounds can be present in the form of salts, such as hydrochloride, phosphate, nitrate.

The above-mentioned compounds of the present invention suppress the gray mold at low concentrations.

When the present compound is used as an antimicrobial agent, it may be admixed with a carrier, and if necessary, with other additives to form a conventional formulation used as an agricultural antimicrobial agent, such as a solid, including finely divided powers and granules materials, as well as a liquid, such as solutions, emulsions, suspensions, concentrates, slurries and the like. Suitable liquid carriers include water; alcohols such as ethanol, ethyleneglycol; ketones such as acetone; ethers such as dioxane, cellosolves; aliphatic hydrocarbons such as kerosene; aromatic hydrocarbons such as benzene, tolvene; organic bases such as pyridine; halogenated hydrocarbons such as chloroform, carbon tetrachloride; esters such as ethyl acetate, fatty acid glycerol esters; nitriles such as acetonitrile; dimethylformamide; and dimethyl sulfoxide.

Suitable solid carriers include powders having a plant origin, such as starches, wheat flour; and mineral powders such as kaolin, bentonite, calcium phosphate, clays, talcs, silicas and the like. These can be used alone or in combination.

Moreover, as the emulsifier, fixing agent, penetrating agent or dispersant, soap, sulfate esters of higher alcohols, alkyl sulfonic acid, alkyl aryl sulfonic acids, tertiary ammonium salts, oxyalkylamines, fatty acid esters, polyalkyleneoxides, and anhydrosolbitols are used. Usually, these additives are used in an amount of 0.2 to 10% by weight relative to the formulation. Further, other antimicrobial agents, insecticides, nematocides, herbicides, plant growth regulators, plant nutrients, fertilizer, and/or soil modifiers can be included in the formulation.

The antimicrobial composition of the present invention can be produced by a conventional procedure from the 2-pyranone derivative (I), carriers, additives and the like.

The present compound (I) is preferably contained in an amount of 0.5 to 50% by weight in a solid formulations, and in an amount of 5 to 90% by weight in a liquid formulation. Note, the liquid for mulations are preferably diluted by an appropriate amount of water, for example, 50 to 5000-fold, prior to application.

An amount of the present compound (I) used, and the ratio thereof to other components in the composition, depends on the stage of growth of a plant to which the composition is to be applied, condition of growth of the plant, a nature of the pathogen, condition of pathology, method of application and the like, and is usually 10 to 300 g of the present compound (I) per 10 acres. A concentration of the compound (I) in a liquid composition in use is usually 10 to 1000 ppm. The method of application of the composition is not particularly limited, and it can be applied by, for example, spraying, dusting or by irrigation, or in the form of a seed coat, as long as it is applied safely and effectively to a target plant.

EXAMPLES

The present invention will be further illustrated by, but is by no means limited to, the following examples.

Example 1

Production of compounds

First, 30 l of a medium containing 90 g glucose, 300 g peptone, 600 g corn starch, 60 g yeast extract, 90 g dry yeast cells, and 30 g dipotasium phosphate (pH 7.0) was inoculated with a pure culture of Streptomyces platensis SAM-0654 (FERM BP-1668), and culturing was carried out in a small fermentor at 28° C., with aeration at 30 l/minute and agitation at 400 rpm, for 40 hours.

The culture broth thus obtained was centrifuged to obtain 27 l of a supernatant, which was then passed through a column (14 cm × 33 cm) packed with Diaion HP-20 (Mitsubishi Chemical Industry Ltd.) to adsorb the product. The column was washed with 30 l of water and 36 l of 50% methanol, and was eluted with 18 l of methanol to obtain an eluate having an anti-Aspergillus (or Botrytis) activity. The eluate was concentrated under reduced pressure, centrifuged to eliminate impurities, and 400 ml of the concentrate was applied to a column (5.6 cm × 33 cm) packed with Sepabeads FP-DA13 (Mitsubishi Chemical Industry Ltd.), which had been washed with methanol, and the column was eluted with methanol. Since an anti-microbial activity was found at an elution volume of 3000 ml to 6600 ml, this fraction was concentrated under a reduced pressure, water was added to the concentrate, and the mixture was lyophilized to obtain 800 mg of a dry preparation. Then 100 mg of the dry preparation was dissolved in methanol, and the solution was applied to a high performance liquid chromatography column (YMC $C_{18}$ column, having an inner diameter of 50 mm and a length of 300 mm; Yamamura Chemical Laboratories Co. Ltd.) Elution was carried out with 40% acetonitrile in 0.1% formic acid for 8 minutes, a linear gradient of 40% to 60% acetonitrile in 0.1% formic acid for 60 minutes, and 60% acetonitrile in 0.1% formic acid for 10 minutes, at a flow rate of 32 ml/minute, while being monitored at an absorbance of 232 nm, and 25.6 ml (0.8 minute) fractions were obtained. This procedure was repeated eight times. The chromatogram thereof is shown in FIG. 1.

Fractions No. 31 to 33 containing peak A provided 13 mg of the above-mentioned compound I-a;

fractions No. 35 to 37 containing peak B provided 50 mg of a mixture comprising the compound I-b and the compound I-c (1:2);

fractions No. 44.to 47 containing peak C provided 120 mg of a mixture comprising the compound I-d and the compound I-e (3:2);

fractions No. 60 to 63 containing peak E provided 119 mg of the compound I-f;

fractions No. 67 to 69 containing peak F provided 35 mg of the compound I-g; and fractions No. 81 to 87 containing peaks H and I provided 84 mg of a mixture comprising the compound I-h, the compound I-i, and the compound I-j (3:2:1).

Further, the mixture comprising the compounds I-a and I-c, the mixture comprising the compounds I-d and I-e, and the mixture comprising the compounds I-h, I-i, and I-j were separately subjected to high performance liquid chromatography under the same conditions as described above, and as a result the compounds I-b and I-c, the compounds I-d and I-e, and the compounds I-h, I-i and I-j were isolated, respectively.

The compounds I-a to I-j thus obtained were white powders that exhibited a maximum ultraviolet absorbance at 232 nm in methanol, had a positive ninhydrin reaction, Ryndon Smith reaction, iodine reaction, anisaldehyde sulfuric acid reaction, and phosphomolybdic acid·perchloric acid reaction, and a negative BTB and p-anisidine reaction. Note, the compound I-j was obtained in only a small amount. The structures and physico-chemical properties of the compounds I-a to I-i are shown in Table 3.

TABLE 3

Structure: lactone ring with $CH_2CH_3$ substituent—CH=CH—C($OH$)—$CH_2CH_2NH_2$,  $OH$—CHCH$_2$CHCH=CHCH=CH—cyclohexyl—R, with $OPO_3H_2$

| Compound | R | Molecular formula | Rf value* | IR spectrum ($\nu cm^{-1}$) | NMR spectrum (in $CD_3OD$, $\delta$ ppm) |
|---|---|---|---|---|---|
| I-a | H | $C_{25}H_{40}O_8NP$ | 0.45 | 2968, 2934, 1730, 1604, 1137 | 7.09(1H, dd, J=10.0, 5.0), 6.26(1H, m), 6.23 (1H, m), 6.08(1H, dd, J=15.5, 6.5), 6.02(1H, dd, J=10.0, 1.5), 5.92(1H, dd, J=15.5, 1.0), 5.4(1H, m), 5.31(1H, m), 5.10(1H, ddd, J=6.5, 5.5, 1.0), 4.95(1H, m), 4.27(1H, ddd, J=10.0, 10.0, 3.0), 3.04(2H, m), 2.56(1H, m), 2.46(1H, m), 2.2(1H, ddd, J=7.0), 1.88(1H, ddd, J=7.0), 1.55–1.76(6H, m), 1.44–1.55 (2H, m), 1.24–1.42(3H, m), 1.04–1.24(3H, m), 0.95(3H, dd, J=7.5) |
| I-b | —OCCH$_2$CH$_2$CH$_3$ (O double bond) | $C_{29}H_{46}O_{10}NP$ | 0.48 | 2968, 2935, 1728, 1603, 1093 | 0.93(3H, t, J=6.2), 0.94(3H, t, J=7.0), 1.04 (1H, m), 1.14(1H, m), 1.29(1H, m), 1.37–1.55 (3H, m), 1.55–1.67(4H, m), 1.72(1H, m), 1.78–1.89(2H, m), 1.89–2.01(2H, m), 2.20 (1H, m), 2.25(2H, t, J=7.2), 2.50–2.70(2H, m), 2.94–3.13(2H, m), 4.29(1H, dt, J=2.0, J=10.0), 4.70(1H, m), 4.95(1H, d, J=10.0), 5.10(1H, dd, J=5.0, J=6.8), 5.31(1H, m), 5.46(1H, m), 5.95(1H, d, J=15.9), 6.02(1H, dd, J=10.0, J=1.5), 6.05(1H, dd, J=6.8, J=15.9), 6.22–6.33(2H, m), 7.08(1H, dd, J=5.5, J=10.2) |
| I-c | —OCCH(CH$_3$)$_2$ | $C_{29}H_{46}O_{10}NP$ | 0.48 | 2968, 2935, 1728, 1603, 1093 | 0.94(3H, t, J=7.0), 1.04(1H, m), 1.12(6H, d, J= 7.0), 1.14(1H, m), 1.29(1H, m), 1.37–1.55 (3H, m), 1.55–1.67(2H, m), 1.72(1H, m), 1.78–1.89(2H, m), 1.89–2.01(2H, m), 2.20(1H, m), 2.49(1H, sep, J=7.0), 2.51–2.69(2H, m), 2.94–3.13(2H, m), 4.29(1H, dt, J=2.0, J=10.0), 4.70(1H, m), 4.95(1H, d, J=10.0), 5.10(1H, dd, J=5.0, J=6.8), 5.31(1H, m), 5.46(1H, m), 5.95(1H, d, J=15.9), 6.02(1H, dd, J=10.0, J=1.5), 6.05(1H, dd, J=6.8, J=15.9), 6.22–6.33(2H, m), 7.08(1H, dd, J=5.5, J=10.2) |
| I-d | —OCCH$_2$CH(CH$_3$)CH$_3$ | $C_{30}H_{48}O_{10}NP$ | 0.49 | 3374, 2872, 1726, 1383, 1294, 1188 | 0.94(6H, d, J=6.7), 0.95(3H, t, J=8.0), 1.05 (1H, m), 1.15(1H, q, J=11.8), 1.28(1H, m), 1.40–1.54(3H, m), 1.57–1.67(2H, m), 1.73 (1H, m) 1.78–1.89(2H, m), 1.91–2.01(2H, m), 2.04(1H, m), 2.15(2H, d, J=7.2), 2.19(1H, m), 2.56(1H, m), 2.63(1H, m), 3.00(1H, m), 3.08 (1H, m), 4.30(1H, dt, J=2.5, J=10.1), 4.73 (1H, m), 4.94(1H, m), 5.10(1H, dd, J=6.6, J=4.7), 5.31(1H, m), 5.46(1H, m), 5.95(1H, d, J=15.6), 6.02(1H, dd, J=10.0, J=1.2), 6.05 (1H, dd, J=15.6, J=6.6), 6.24–6.32(2H, m), 7.08(1H, dd, J=10.0, J=5.0) |
| I-e | —OCCH(CH$_3$)CH$_2$CH$_3$ | $C_{30}H_{48}O_{10}NP$ | 0.49 | 3374, 2872, 1726, 1383, 1294, 1188 | 0.89(3H, t, J=7.5), 0.95(3H, t, J=8.0), 1.05 (1H, m), 1.10(3H, d, J=6.9), 1.15(1H, q, J= 11.8), 1.28(1H, m), 1.40–1.54(4H, m), 1.57–1.67(3H, m), 1.73(1H, m), 1.78–1.89(2H, m), 1.91–2.01(2H, m), 2.19(1H, m), 2.32(1H, m), 2.56(1H, m), 2.63(1H, m), 3.00(1H, m), 3.08 (1H, m), 4.30(1H, dt, J=2.5, J=10.1), 4.73(1H, m), 4.94(1H, m), 5.10(1H, dd, J=10.0, J=1.2), 6.05(1H, dd, J=15.6, J=6.6), 6.24–6.32(2H, m), 7.08(1H, dd, J=10.0, J=5.0) |

TABLE 3-continued

Structure at top of table:
$CH_2CH_3$ group on ring; $CH_2CH_2NH_2$, $OH$, $OPO_3H_2$ groups on chain:
—CH=CH—C(CH$_2$CH$_2$NH$_2$)(OH)—CHCH$_2$CH(OPO$_3$H$_2$)CH=CHCH=CH—[cyclohexyl]—R
(with pyranone ring containing ethyl substituent on left)

| Compound | R | Molecular formula | Rf value* | IR spectrum (νcm⁻¹) | NMR spectrum (in CD$_3$OD, δ ppm) |
|---|---|---|---|---|---|
| I-f | —OC(=O)—cyclohexyl | $C_{32}H_{50}O_{10}NP$ | 0.50 | 3455, 2932, 1722, 1451, 1383, 1318, 1246, 1173 | 0.95(3H, t, J=7.5), 1.05(1H, m), 1.14(1H, q, J=11.8), 1.19-1.36(4H, m), 1.36-1.54(5H, m), 1.58-1.67(3H, m), 1.68-1.76(3H, m), 1.79-1.87(4H, m), 1.90-1.98(2H, m), 2.20(1H, m), 2.26(1H, m), 2.55(1H, m), 2.62(1H, m), 3.01 (1H, m), 3.07(1H, m), 4.29(1H, dt, J=2.4, J=10.1), 4.69(1H, m), 4.94(1H, m), 5.10(1H, dd, J=4.7, J=6.7), 5.31(1H, m), 5.46(1H, m), 5.96(1H, d, J=15.6), 6.02(1H, dd, J=1.3, J=9.8), 6.06(1H, dd, J=6.7, J=15.6), 6.23-6.32 (2H, m), 7.08(1H, dd, J=5.1, J=9.8) |
| I-g | —O—C(=O)—(CH$_2$)$_2$CH(CH$_3$)CH$_2$CH$_3$ | $C_{32}H_{52}O_{10}NP$ | 0.50 | 3358, 2963, 1726, 1711, 1464, 1450, 1383, 1253 | 0.84-0.91(6H, m), 0.95(3H, t, J=7.4), 0.98-1.23(3H, m), 1.23-1.55(7H, m), 1.55-1.77(4H, m), 1.77-1.89(2H, m), 1.89-2.02(2H, m), 2.15-2.35(3H, m), 2.51-2.68(2H, m), 2.95-3.13(2H, m), 4.28(1H, dt, J=2.0, J=10.0), 4.71 (1H, m), 4.93(1H, m), 5.09(1H, dd, J=5.2, J=6.4), 5.31(1H, m), 5.45(1H, m), 5.94(1H, d, J=15.6), 6.01(1H, d, J=9.8), 6.05(1H, dd, J=6.4, J=15.6), 6.22-6.33(2H, m), 7.08(1H, dd, J=9.8, J=5.1) |
| I-h | —O—C(=O)—(CH$_2$)$_4$—CH(CH$_3$)CH$_3$ | $C_{33}H_{54}O_{10}NP$ | 0.52 | 2935, 2865, 1730, 1240, 1174, 1057 | 0.88(6H, d, J=6.7), 0.95(3H, t, J=7.5), 1.04 (1H, m), 1.10-1.22(3H, m), 1.23-1.36(3H, m), 1.39-1.67(8H, m), 1.72(1H, t, J=12.2), 1.79-1.89(2H, m), 1.91-2.03(2H, m), 2.17-2.25 (1H, m), 2.27(2H, t, J=7.4), 2.55(1H, m), 2.62 (1H, m), 3.01(1H, m), 3.08(1H, m), 4.30(1H, t, J=9.4), 4.72(1H, m), 4.94(1H, m), 5.10(1H, m), 5.31(1H, m), 5.46(1H, m), 5.95(1H, d, J=15.6), 6.02(1H, dd, J=9.8, J=1.2), 6.05(1H, dd, J=15.6, J=6.6), 6.23-6.32(2H, m), 7.08 (1H, dd, J=9.8, J=5.1) |
| I-i | —O—C(=O)—(CH$_2$)$_6$CH$_3$ | $C_{33}H_{54}O_{10}NP$ | 0.52 | 2930, 2867, 1730, 1250, 1170, 1057 | 0.90(3H, t, J=7.0), 0.95(3H, t, J=7.5), 1.05 (1H, m), 1.15(1H, q, J=11.8), 1.19-1.37(8H, m), 1.38-1.54(4H, m), 1.54-1.76(5H, m), 1.79-1.89(2H, m), 1.91-2.01(2H, m), 2.17-2.25(1H, m), 2.27(2H, t, J=7.3), 2.55(1H, m), 2.62(1H, m), 3.01(1H, m), 3.08(1H, m), 4.30 (1H, dt, J=9.2, J=1.0), 4.72(1H, m), 4.94(1H, m), 5.10(1H, m), 5.31(1H, m), 5.46(1H, m), 5.95(1H, d, J=15.5), 6.02(1H, dd, J=9.8, J=1.1), 6.05(1H, dd, J=15.5, J=6.6), 6.23-6.33 (2H, m), 7.08(1H, dd, J=9.8, J=5.1) |

*Silica gel thin layer chromatography (Merck HPTLC Silica F254; developing solvent = chroloform/methanol/water 6:4:1; detected by bioautography using *Aspergillus oryzae*, anisaldehyde-sulfuric acid reaction and ninhydrin reaction.

Test for anti-fungal activity

The disease suppressive activity of the present compounds I-a, I-c (and I-b), I-d (and I-e), I-f, I-g, I-h, and I-i against the gray mold was tested by the following procedure. A solution of the present compound having a predetermined concentration was coated with an absorbent cotton block to cotyledon of a cucumber seedling seven days after seeding. One day after the coating, an agar disk having a diameter of 5 mm containing *Botrytis cinerea* was put on the coated cotyledon, the plant was incubated at 20° C. for three days, and the disease suppressive activity of the tested compound was observed. The results are shown in Table 4. In Table 4, *Botrytis cinerea* RR-4 is a strain resistant to antimicrobial agents (multi-resistant strain), isolated from a diseased seedling of egg plant, and *Botrytis cinerea* S-9 is a strain sensitive to antimicrobial agents, isolated from a diseased petal of orange blossom. Note, the extent of the disease suppressive effect is expressed by symbols + (no lesion), ± (lesion having a diameter of less than 10 mm formed), and − (lesion having a diameter of not less than 10 mm formed.)

TABLE 4

| Test compound | Disease suppressive effect to *Botrytis cinerea* | | |
|---|---|---|---|
| | Concentration (ppm) | *Botrytis cinerea* S-9 | *Botrytis cinerea* RR-4 |
| I-a | 125 | + | + |
| | 32 | − | − |
| I-b and I-c (1:2) | 125 | + | + |
| | 32 | ± | ± |
| I-d and I-e | 125 | + | + |

TABLE 4-continued

| | | Disease suppressive effect to *Botrytis cinerea* | |
|---|---|---|---|
| Test compound | Concentration (ppm) | *Botrytis cinerea* S-9 | *Botrytis cinerea* RR-4 |
| (3:2) | 32 | ± | ± |
|  | 8 | − | − |
| I-f | 32 | + | + |
|  | 8 | + | + |
| I-g | 32 | + | + |
|  | 8 | + | + |
| I-h | 32 | + | + |
|  | 8 | − | − |
| I-i | 32 | + | + |
|  | 8 | − | − |
| Procymidone | 125 | + | − |
|  | 32 | − | − |
| No treatment |  | − | − |

We claim:

1. A 2-pyranone derivative represented by the formula (I):

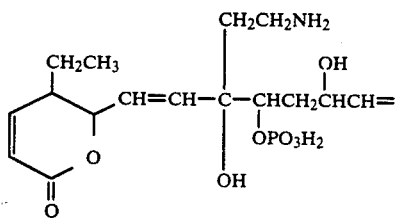

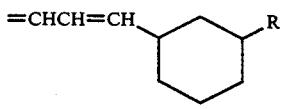

wherein R represents a hydrogen atom, or a linear, or branched aklylcarbonyloxy, cyclohexylethylcarbonyloxy or cyclo-alkylcarbonyloxy group having 3 to 10 carbon atoms, and salts thereof.

2. A 2-pyranone derivative according to claim 1, wherein the alkylcarbonyloxy is selected from a group consisting of butyryloxy, isobutyryloxy, isovaleryloxy, 2-methylbutyryloxy, cyclohexylcarbonyloxy, 4-methylhexanoyloxy, 6-methylheptanoyloxy, and octanoyloxy.

3. A biocidal composition comprising a 2-pyranone derivative according to claim 1.

4. A 2-pyranone derivative according to claim 1, wherein R represents a hydrogen atom.

5. A 2-pyranone derivative according to claim 1, wherein R represents n-butyryloxy.

6. A 2-pyranone derivative according to claim 1, wherein R represents isobutyryloxy.

7. A 2-pyranone derivative according to claim 1, wherein R represents isovaleryloxy.

8. A 2-pyranone derivative according to claim 1, wherein R represents 2-methylbutyryloxy.

9. A 2-pyranone derivative according to claim 1, wherein R represents cyclohexylcarbonyloxy.

10. A 2-pyranone derivative according to claim 1, wherein R represents 4-methylhexanoyloxy.

11. A 2-pyranone derivative according to claim 1, wherein R represents 6-methylheptanoyloxy.

12. A 2-pyranone derivative according to claim 1, wherein R represents octanoyloxy.

13. A 2-pyranone derivative according to claim 1, wherein R represents cyclohexylethylcarbonyloxy.

* * * * *

UNITED STATES PATENT AND TRADEMARK OFFICE
CERTIFICATE OF CORRECTION

PATENT NO. : 5,021,406

DATED : June 4, 1991

INVENTOR(S) : Mitsuru MAEDA et al

It is certified that error appears in the above-identified patent and that said Letters Patent is hereby corrected as shown below:

ON THE TITLE PAGE:

[30] Foreign Application Priority Data, please insert the following:

Feb. 7, 1989 [JP]   Japan................ 1-26657

Signed and Sealed this

Fifteenth Day of December, 1992

*Attest:*

DOUGLAS B. COMER

*Attesting Officer*   *Acting Commissioner of Patents and Trademarks*